United States Patent [19]
Hammang et al.

[11] Patent Number: 6,027,721
[45] Date of Patent: Feb. 22, 2000

[54] DEVICE AND METHOD FOR ENCAPSULATED GENE THERAPY

[75] Inventors: Joseph P. Hammang, Barrington, R.I.; Patrick Aebischer, Lutry, Switzerland

[73] Assignee: Cytotherapeutics, Inc., Lincoln, R.I.

[21] Appl. No.: 08/650,726

[22] Filed: May 20, 1996

[51] Int. Cl.$^7$ .......................... C12N 15/85; C12N 15/00; A61K 48/00; A61K 9/48

[52] U.S. Cl. .................. 424/93.2; 424/452; 435/325; 435/465; 514/44

[58] Field of Search .......................... 514/44; 424/93.1, 424/93.21, 93.2, 452; 435/325, 465

[56] References Cited

U.S. PATENT DOCUMENTS

| | | | |
|---|---|---|---|
| 3,615,024 | 10/1971 | Michaels | 210/490 |
| 4,353,888 | 10/1982 | Sefton | 424/25 |
| 4,530,901 | 7/1985 | Weissmann | 435/70 |
| 4,588,585 | 5/1986 | Mark et al. | 424/85 |
| 4,629,563 | 12/1986 | Wrasidlo | 210/500.34 |
| 4,861,719 | 8/1989 | Miller | 435/236 |
| 4,868,116 | 9/1989 | Morgan et al. | 435/240.2 |
| 4,892,538 | 1/1990 | Aebischer et al. | 604/891.1 |
| 4,935,141 | 6/1990 | Buck et al. | 210/500.38 |
| 4,968,733 | 11/1990 | Müller et al. | 521/64 |
| 4,976,859 | 12/1990 | Wechs | 210/500.23 |
| 4,980,286 | 12/1990 | Morgan et al. | 435/172.3 |
| 5,011,472 | 4/1991 | Aebischer et al. | 604/50 |
| 5,026,365 | 6/1991 | Rossini et al. | 604/891.1 |
| 5,158,881 | 10/1992 | Aebischer et al. | 435/182 |
| 5,219,740 | 6/1993 | Miller et al. | 435/69.6 |
| 5,288,846 | 2/1994 | Quertermous et al. | 435/172.3 |
| 5,326,859 | 7/1994 | Sugano et al. | 536/23.52 |
| 5,399,346 | 3/1995 | Anderson et al. | 424/93.21 |
| 5,401,410 | 3/1995 | Bell et al. | 210/500.41 |
| 5,449,614 | 9/1995 | Danos et al. | 435/172.3 |
| 5,453,368 | 9/1995 | Tresco et al. | 435/112 |
| 5,460,959 | 10/1995 | Mulligan et al. | 435/172.3 |
| 5,487,739 | 1/1996 | Aebischer et al. | 604/890.1 |
| 5,529,774 | 6/1996 | Barba et al. | 424/93.21 |
| 5,529,914 | 6/1996 | Hubbell et al. | 435/182 |
| 5,550,050 | 8/1996 | Holland et al. | 435/240.2 |
| 5,573,528 | 11/1996 | Aebischer et al. | 604/891.1 |

FOREIGN PATENT DOCUMENTS

| | | |
|---|---|---|
| 356 045 | 9/1995 | European Pat. Off. . |
| 342 026 | 10/1995 | European Pat. Off. . |
| 675 200 | 10/1995 | European Pat. Off. . |
| WO 90/15637 | 12/1990 | WIPO . |
| WO 91/01720 | 2/1991 | WIPO . |
| WO 92/07943 | 5/1992 | WIPO . |
| WO 92/19195 | 11/1992 | WIPO . |
| WO 93/00127 | 1/1993 | WIPO . |
| WO 94/15663 | 7/1994 | WIPO . |
| WO 94/29437 | 12/1994 | WIPO . |
| WO 95/23598 | 9/1995 | WIPO . |
| WO 95/24467 | 9/1995 | WIPO . |
| WO 95/24929 | 9/1995 | WIPO . |
| WO 95/26411 | 10/1995 | WIPO . |
| WO 95/27512 | 10/1995 | WIPO . |
| WO 95/30761 | 11/1995 | WIPO . |
| WO 95/32298 | 11/1995 | WIPO . |
| WO 95/32627 | 12/1995 | WIPO . |
| WO 95/33842 | 12/1995 | WIPO . |

OTHER PUBLICATIONS

Asai, A. et al., "Modulation of Tumor Immunogenicity of Rat Glioma Cells by s–Myc Expression: Eradication of Rat Gliomas in Vivo," *Cell Growth & Differentiation*, 5, pp. 1153–1158 (1994).

Barba, D. et al., "Development of Anti–Tumor Immunity Following Thymidine Kinase–Mediated Killing of Experimental Brain Tumors," *Proc. Natl. Acad. Sci. USA*, 91, pp. 4348–4352 (1994).

Barba, D. et al., "Thymidine Kinase–Mediated Killing of Rat Brain Tumors," *Journal of Neurosurgery*, 79, pp. 729–735 (1993).

Brunauer, S. et al., "Adsorption of Gases in Multimolecular Layers," *The Journal of the American Chemical Society*, 60, pp. 309–319 (1938).

Cabasso, I. et al., "Polysulfone Hollow Fibers. I. Spinning and Properties," *Journal of Applied Polymer Science*, 20, pp. 2377–2394 (1976).

Chambers, R. et al., "Comparison of Genetically Engineered Herpes Simplex Viruses for the Treatment of Brain Tumors in a scid Mouse Model of Human Malignant Glioma," *Proc. Natl. Acad. Sci. USA*, 92, pp. 1411–1415 (1995).

Chen, L. and Waxman, D.J., "Intratumoral Activation and Enhanced Chemotherapeutic Effect of Oxazaphosphorines Following Cytochrome P–450 Gene Transfer: Development of a Combined Chemotherapy/Cancer Gene Therapy Strategy," *Cancer Research*, 55, pp. 581–589 (1995).

Chiocca, E.A. et al., "Virus–Mediated Genetic Treatment of Rodent Gliomas," *Gene Therapeutics: Methods and Applications of Direct Gene Transfer*, pp. 245–262 (Jon A. Wolff, ed., 1994).

Chomczynski, P. and Sacchi, N., "Single–Step Method of RNA Isolation by Acid Guanidinium Thiocyanate–Phenol–Chloroform Extraction," *Analytical Biochemistry*, 162, pp. 156–159 (1987).

Culver, K.W. et al., "Gene Therapy for the Treatment of Malignant Brain Tumors with in Vivo Tumor Transduction with the Herpes Simplex Thymidine Kinase Gen/Ganciclovir System," *Human Gene Therapy*, 5, pp. 343–379 (1994).

Culver, K.W. et al., "In Vivo Gene Transfer with Retroviral Vector–Producer Cells for Treatment of Experimental Brain Tumors," *Science*, 256, pp. 1550–1552 (1992).

Davis, B.D., *Microbiology: Including Immunology and Molecular Genetics*, pp. 874–877 (Harper & Row, 3d ed. 1980).

(List continued on next page.)

*Primary Examiner*—Bruce R. Campell
*Assistant Examiner*—Deborah J. R. Clark
*Attorney, Agent, or Firm*—Mintz, Levin, Cohn, Ferris, Glovsky and Popeo, P.C.; Ivon R. Elrifi; John T. Prince

[57] ABSTRACT

Methods and devices are provided for gene therapy using encapsulated packaging cell lines to deliver viral particles carrying at least one heterologous gene encoding at least one biologically active molecule.

21 Claims, 2 Drawing Sheets

OTHER PUBLICATIONS

Ezzeddine, Z.D. et al., "Selective Killing of Glioma Cells in Culture and in Vivo by Retrovirus Transfer of the Herpes Simplex Virus Thymidine Kinase Gene," *The New Biologist*, 3, 6, pp. 608–614 (1991).

Gandelman, K. et al., "Analysis of the Structure and Expression of the Human Dopamine $D2_A$ Receptor Gene," *Journal of Neurochemistry*, 56, 3, pp. 1024–1029 (1991).

Gruber, S.A., "The Case for Local Immunosuppression," *Transplantation*, 54, 1, pp. 1–11 (1992).

Hajihosseini, M. et al., "Evidence that Retroviruses Integrate into Post–Replication Host DNA," *The EMBO Journal*, 12, 13, pp. 4969–4974 (1993).

Izquierdo, M. et al., "Long–Term Rat Survival after Malignant Brain Tumor Regression by Retroviral Gene Therapy," *Gene Therapy*, 2, 1, pp. 66–69 (1995).

Kasahara, N. et al., "Tissue–Specific Targeting of Retroviral Vectors through Ligand–Receptor Interactions," *Science*, 266, pp. 1373–1376 (1994).

Krug, M.S. and Berger, S.L., "First–Strand cDNA Synthesis Primed with Oligo(dT)," *Methods in Enzymology*, 152, pp. 316–325 (1987).

Linskey, M.E. and Gilbert, M.R., "Glial Differentiation: A Review with Implications for New Directions in Neuro–Oncology," *Neurosurgery*, 36, 1, pp. 1–22 (1995).

Miyao, Y. et al., "Selective Expression of Foreign Genes in Glioma Cells: Use of the Mouse Myelin Basic Protein Gene Promoter to Direct Toxic Gene Expression," *Journal of Neuroscience Research*, 36, pp. 472–479 (1993).

Nabel, G.J. et al., "Immunotherapy of Malignancy by in Vivo Gene Transfer into Tumors," *Human Gene Therapy*, 3, pp. 399–410 (1992).

Nelsen, F.M. and Eggersten, F.T., "Determination of Surface Area: Adsorption Measurements by a Continuous Flow Method," *Analytical Chemistry*, 30, 8, pp. 1387–1390 (1958).

Oldfield, E.H. et al., "Gene Therapy for the Treatment of Brain Tumors Using Intra–Tumoral Transduction with the Thymidine Kinase Gene and Intravenous Ganciclovir," *Human Gene Therapy*, 4, pp. 39–69 (1993).

Ram, Z. et al., "The Effect of Thymidine Kinase Transduction and Ganciclovir Therapy on Tumor Vasculature and Growth of 9L Gliomas in Rats," *Journal of Neurosurgery*, 81, pp. 256–260 (1994).

Ram, Z. et al., "In Situ Retroviral–Mediated Gene Transfer for the Treatment of Brain Tumors in Rats," *Cancer Research*, 53, pp. 83–88 (1993).

Short, M.P. et al., "Gene Delivery to Glioma Cells in Rat Brain by Grafting of a Retrovirus Packaging Cell Line," *Journal of Neuroscience Research*, 27, pp. 427–439 (1990).

Smith, F. et al., "Virus Vectors for Gene Delivery to the Nervous System," *Restorative Neurology and Neuroscience*, 8, pp. 21–34 (1995).

Somia, N.V. et al., "Generation of Targeted Retroviral Vectors by Using Single–Chain Variable Fragment: An Approach to in Vivo Gene Delivery," *Proc. Natl. Acad. Sci. USA*, 92, pp. 7570–7574 (1995).

Strathmann, H. et al., "The Formation Mechanism of Asymmetric Membranes," *Desalination*, 16, pp. 179–203 (1975).

Strathmann, H., "Production of Microporous Media by Phase Inversion Processes," *Materials Science of Synthetic Membranes*, ACS Symposium Series 269, pp. 165–195 (1985).

Takamiya, Y. et al., "An Experimental Model of Retrovirus Gene Therapy for Malignant Brain Tumors," *Journal of Neurosurgery*, 79, pp. 104–110 (1993).

Takamiya, Y. et al., "Gene Therapy of Malignant Brain Tumors: A Rat Glioma Line Bearing the Herpes Simplex Virus Type 1–Thymidine Kinase Gene and Wild Type Retrovirus Kills Other Tumor Cells," *Journal of Neuroscience Research*, 33, pp. 493–503 (1992).

Tamiya, T. et al., "Transgene Inheritance and Retroviral Infection Contribute to the Efficiency of Gene Expression in Solid Tumors Inoculated with Retroviral Vector Producer Cells," *Gene Therapy*, 2, pp. 531–538 (1995).

Tjuvajev, J. et al., "RG–2 Glioma Growth Attenuation and Severe Brain Edema Caused by Local Production of Interleukin–2 and Interferon–$\gamma$," *Cancer Research*, 55, pp. 1902–1910 (1995).

Weller, M. et al., "Fas/APO–1 Gene Transfer for Human Malignant Glioma," *Cancer Research*, 55, pp. 2936–2944 (1995).

Wu, J.K. et al., "Bystander Tumoricidal Effect in the Treatment of Experimental Brain Tumors," *Neurosurgery*, 35, 6, pp. 1094–1103 (1994).

Yamada, M. et al., "Retrovirus–Mediated Gene Transfer Targeted to Malignant Glioma Cells in Murine Brain," *Jpn. J. Cancer Res.*, 83, pp. 1244–1247 (1992).

Aebischer et al. Transplantation of neural tissue im polymer capsules, Brain Res vol. 448, pp. 364–368, 1988.

Baetge et al. Delivery of a putative Parkinson's factor (GDNF) into the rat CNS using a polymer–encapsulate cell line. 33rd annual meeting of the American Society for cell biology. No. 2567, 1993.

Zurn et al. Glial Cell line–derived neurotrophic factor (GDNF), a new neurotropic factor for motoneurones, Neuroreport vol. 6 No. 1 pp. 113–118, Dec. 30, 1994.

Christenson et al. Encapsulated thymic stromal cells enhance proliferation of CD4–CD8– thymocytes, joint meeting of the American society for biochemistry and molecular biology and the American association of immunologists. No. 192, Jun. 1990.

Emerich et al, Transplantation of Polymer–encapsulated cells genetically modified to secrete human nerve degenerating cholinergic neurons in rats and nonhuman primates. 2nd International Congress of the Cell transport society. No. 3, 1994.

Hammang et al, Delivery of neurotrophic factors to the CNS using encapsulated cells: developing treatments for neurodegenerative diseases. Cell Transplantation, vol. 4, pp. s27–s28, 1995.

Winn et al, Development of a polymer–encapsulated cellular implant for pain modulation. 23rd annual meeting of the society for neuroscience. No. 577.1, 1993.

Sagot et al, Polymer encapsulated cell lines secreting neurotrophic factors can rescue montoneurons in an animal model of motoneuron disease. 24th annual meeting of the society for neuroscience. No. 87.7, 1994.

NIH panel, Report and Recommendations of the panel to assess the NIH investment in research on gene therapy, Dec. 7, 1995.

Friedman, Theodore. Gene Therapy for neurological disorders. TIG vol. 10, No. 6, pp. 210–214, Jun. 1994.

DEVICE AND METHOD FOR ENCAPSULATED GENE THERAPY

FIELD OF THE INVENTION

This invention relates to devices and methods for site specific in vivo gene therapy using encapsulated cells releasing gene transfer vectors.

BACKGROUND OF THE INVENTION

Broadly, gene therapy seeks to transfer new genetic material to the cells of a patient with resulting therapeutic benefit to the patient. Such benefits include treatment or prophylaxis of a broad range of diseases, disorders and other conditions.

Ex vivo gene therapy approaches involve modification of isolated cells, which are then infused, grafted or otherwise transplanted into the patient. See, e.g., U.S. Pat. Nos. 4,868,116, 5,399,346 and 5,460,959. In vivo gene therapy seeks to directly target host patient tissue in vivo.

Viruses useful as gene transfer vectors include papovavirus, adenovirus, vaccinia virus, adeno-associated virus, herpesvirus, and retroviruses.

Retroviral vectors are the vectors most commonly used in human clinical trials, since they carry a larger genetic payload than other viral vectors and they have the ability to infect cells and have their genetic material stably integrated into the host cell with high efficiency. See, e.g., WO 95/30761; WO 95/24929. Retroviruses require at least one round of target cell proliferation for transfer and integration of exogenous nucleic acid sequences into the patient. Retroviral vectors integrate randomly into the patient's genome.

Two classes of retroviral particles have been described; ecotropic, which can infect murine cells efficiently, and amphotropic, which can infect cells of many species. Their ability to integrate only into the genome of dividing cells has made retroviruses attractive for marking cell lineages in developmental studies and for delivering therapeutic or suicide genes to cancers or tumors. These vectors may be particularly useful in the central nervous system, where there is a relative lack of cell division in adult patients.

Retroviruses consist of a protein envelope that surrounds core proteins and RNA. The RNA encodes two long terminal repeats (LTRs), which include promoter and enhancer regions flanking the genome, transcriptional regulatory signals including the CAP site and polyadenylation signals, and structural genes including the env gene (encoding the envelope proteins), the gag gene (encoding the viral core proteins), and the pol gene (encoding the reverse transcriptase), as well as the packaging signal, psi ($\psi$).

For use in human patients, the retroviral vectors must be replication defective. This prevents further generation of infectious retroviral particles in the target tissue—instead the replication defective vector becomes a "captive" transgene stable incorporated into the target cell genome. Typically in replication defective vectors, the gag, env, and pol genes have been deleted (along with most of the rest of the viral genome). Heterologous DNA is inserted in place of the deleted viral genes. The heterologous genes may be under the control of the endogenous heterologous promoter, another heterologous promoter active in the target cell, or the retroviral 5' LTR (the viral LTR is active in diverse tissues). Typically, retroviral vectors have a transgene capacity of about 7–8 kb.

Replication defective retroviral vectors require provision of the viral proteins necessary for replication and assembly in trans, from, e.g., engineered packaging cell lines. It is important that the packaging cells do not release replication competent virus and/or helper virus. This has been achieved by expressing viral proteins from RNAs lacking the $\psi$ signal, and more recently, expressing the gag/pol genes and the env gene from separate transcriptional units. In addition, in some packaging cell lines, the LTR's have been replaced with non-viral promoters and polyadenylation signals. These designs minimize the possibility of recombination leading to production of replication competent vectors, or helper viruses. See, e.g., U.S. Pat. No. 4,861,719, herein incorporated by reference.

Current gene therapy approaches are unsatisfactory. First, direct introduction of retroviral vectors into the host, by injection, or via liposome delivery, has several limitations. Because of their low titer and instability, a single infusion of viral vectors may be insufficient to result in infection (and gene transfer) to 100% of the desired host target tissue.

Second, use of an externalized shunt or tube is not optimal because the externalized tube or shunt could lead to infections in the patient, particularly in the brain if the treatment site is in the central nervous system ("CNS"). In addition, this is a very difficult approach for delivery to the brain parenchyma.

Third, current methods of in vivo gene therapy do not readily allow termination of, or adjustments to, the gene therapy protocol once the viral vectors have been introduced into the patient.

Certain gene therapy protocols have called for grafting of retrovirus packaging cell lines into the rodent brain for the treatment of glioblastoma. The packaging cells then release replication-incompetent retroviral particles containing genes that are desirably transferred to the tumor cells. See, e.g., Takamiya et al., J. Neurosurg., 79, pp. 104–110 (1993); Short et al., J. Neuroscience Res., 27, pp. 427–33 (1990). This method too has several limitations in human patients.

First, the injection of $10^9$ (or less) xenogeneic (or even allogeneic) packaging cells can create a severe immune reaction, requiring immunosuppression of the patient.

Second, a single "graft" of virus-producing cells may not be sufficient to provide the necessary number of viral particles over a biologically significant time course to kill the targeted tumor cells. The grafted packaging cells are likely to be rejected by the patient's immune system within about 7 days. Vector production may only occur for a significantly shorter period of time. It would be unlikely that 100% of the tumor cells would be infected after this limited duration. In addition, the severe immune reaction that is likely to result from the first injection may preclude subsequent injection(s) of cells that may be necessary for complete treatment. The potential reaction to such subsequent injections could prove to be dangerous or fatal.

Third, there is no mechanism in current protocols to prevent unencapsulated packaging cells from migrating in situ. The inability to retain implanted cells in a fixed location may make "naked" packaging cells unsuitable as therapeutic agents because of the possibility that the packaging cells themselves could be tumorigenic. Implantation of naked packaging cell lines is particularly a problem in immunosuppressed patients, because in those patients the immune system has a reduced ability to destroy the packaging cells should they become tumorigenic. Further, the ability of naked packaging cells to migrate increases the chances of inadvertent infection of dividing host tissues in various regions outside the CNS.

Fourth, because the grafted packaging cells in the patient are not well isolated from the patient's own tissue, they cannot be readily retrieved or manipulated, and thus do not allow termination of, or adjustments to, the gene therapy protocol once the cells are implanted.

It would be useful to provide devices and methods of gene therapy for the localized in vivo continuous delivery of viral vector particles, while preventing or reducing in situ migration of the viral vectors or packaging cells. It is also desirable to provide devices and methods of gene therapy with a reduced likelihood of eliciting an immune response in the patient. It is further desirable to provide devices and methods that permit a repeatable therapy, that can be easily and rapidly adjusted or terminated.

SUMMARY OF THE INVENTION

The devices and methods of this invention provide for the delivery of viral particles to a desired site in a patient using a capsular approach. Encapsulation of vector-producing cell lines permits continuous delivery of the viral particle to the target site, as opposed to a single infusion. In addition, repeat therapy is possible, with reduced likelihood of immune attack. The capsules have pores large enough to allow passage of viral particles released from the packaging cells, yet prevent host-cell passage into the capsule.

This capsular approach increases the safety and control of the therapy because the devices can easily be retrieved (terminating the treatment) or explanted and reimplanted (modifying the treatment). Further, the chance of infection is reduced because the capsular device is not open or externalized.

Finally, because encapsulation prevents the packaging cells from migrating within the patient, and prolongs the viability of the packaging cells upon implant, fewer cells are likely to be needed for this therapy. This may be advantageous in further lowering an immune reaction in the patient.

DETAILED DESCRIPTION OF THE INVENTION

The instant invention provides biocompatible encapsulation devices and methods of using them for encapsulating vector-producing cells, thereby allowing the release of viral particles for the delivery of genetic material to patient cells. The capsules also allow for the efficient adjustment or termination of gene therapy regimes. Specifically, the jackets of the capsules of this invention comprise membranes that permit passage of viral particles therethrough, thereby permitting infection of target host tissue.

The capsules of this invention can be manufactured using the methods and materials disclosed in WO 92/19195. Briefly, the capsule is comprised of (a) a core containing isolated packaging cells, either suspended in a liquid medium or immobilized within a biocompatible matrix, and (b) a biocompatible surrounding or peripheral region ("jacket") of a material that permits passage of the viral particles therethrough.

The core of the capsule is constructed to allow for appropriate release of the viral vector. Where packaging cells are encapsulated, the core provides a suitable local environment for the continued viability and function of the packaging cells isolated therein. In some embodiments, the core comprises a liquid medium sufficient to maintain the cells. In such cases, the core may also comprise a liquid source of additional factors to sustain cell viability and function. In other embodiments, the core comprises a biocompatible matrix that immobilizes and evenly distributes the packaging cells, thereby reducing the formation of dense cellular agglomerations.

We prefer a biocompatible matrix core comprising a hydrogel. The term "hydrogel" herein refers to a three dimensional network of cross-linked hydrophilic polymers. The network is in the form of a gel, substantially composed of water, preferably but not limited to gels being greater than 90% water. Compositions which form hydrogels fall into three classes. The first class carries a net negative charge (e.g., alginate). The second class carries a net positive charge (e.g., collagen and laminin). Examples of commercially available extracellular matrix components include Matrigel™ and Vitrogen™. The third class is net neutral in charge (e.g., highly crosslinked polyethylene oxide, or polyvinylalcohol). Any other suitable matrix or spacer also may be employed within the core, including precipitated chitosan, synthetic polymers and polymer blends, microcarriers and the like.

The jacket of the capsule is formed from any suitable biocompatible material. The biocompatibility of the jacket means that it does not upon implantation into the patient elicit a detrimental immune response sufficient to result in rejection of the implanted capsule or to render it inoperable, for example, through degradation. It also means that the jacket does not elicit unfavorable tissue responses. In addition, the external surface can be selected or designed in such a manner that it is particularly suitable for implantation at the selected site. For example, the external surface can be smooth, stippled or rough, depending on whether attachment by cells of the surrounding tissue is desirable. The shape or configuration can also be selected or designed to be particularly appropriate for the implantation site chosen.

The capsule can be any configuration appropriate for maintaining biological activity of the packaging cells and providing access for delivery of the viral particles, including, for example, cylindrical, rectangular, disk-shaped, patch-shaped, ovoid, stellate, or spherical. Moreover, the capsule can be coiled or wrapped into a mesh-like or nested structure. Certain shapes, such as rectangles, patches, disks, cylinders and flat sheets offer greater structural integrity and are preferable where retrieval is desired.

Although microcapsular devices are contemplated (see, e.g., U.S. Pat. No. 4,353,888, incorporated herein by reference), we prefer that the device is of a sufficient size and durability for complete retrieval after implantation. Such macrocapsules have a core of a preferable minimum volume of about 1 to 10 $\mu$l and depending upon use are easily fabricated to have a volume in excess of 100 $\mu$l. Macrocapsular devices with a core of cells encapsulated in microspheres is specifically contemplated.

In a hollow-fiber configuration, the fiber will have an inside diameter of less than 1500 microns, preferably about 300–600 microns.

The jacket can be made of any suitable material, including hydrogels or thermoplastics. See, e.g., WO 92/19195. It can also be made of a matrix-membrane composite, such that a permselective thermoplastic membrane having matrix-filled pores, such as hydrogel-filled pores, is formed.

Preferably, the external jacket is formed from a biocompatible thermoplastic material. Various polymers and polymer blends can be used to manufacture the capsule jacket, including polyacrylates (including acrylic copolymers), polyvinylidenes, polyvinyl chloride copolymers, polyurethanes, polystyrenes, polyamides, cellulose acetates, cellulose nitrates, polysulfones (including polyether sulfones), polyphosphazenes, polyacrylonitriles, poly (acrylonitrile/covinyl chloride), as well as derivatives, copolymers and mixtures thereof. We prefer microporous polyether sulfone membranes, such as those manufacured by Akzo-Nobel, Wuppertal, Germany.

For ease of retrieval, the capsules preferably have one or more tethers to allow location and grasping of the device without damage to it. Additionally, the tether can be used to find the implanted macrocapsule when it is desirous to terminate therapy, by inclusion of a radioopaque marker, or other suitable identification means. Tethers may be made, for example, according to the methods of Aebischer et al., PCT US92/05369. Suitable tether material is commercially available from Specialty Silicone Fabricators (Robles, Calif.).

The capsule can be formed by coextrusion or in a stepwise fashion. Techniques for coextrusion, are taught for example, in U.S. Pat. No. 5,158,881, herein incorporated by reference. The capsule can also be formed step-wise. For example, if the capsule being made includes a matrix core containing the isolated cells, the core can be formed initially, and the surrounding jacket can be assembled or applied subsequently. Conversely, the jacket can be preformed, and then filled with the cell-containing core material. See, e.g., WO 92/19195.

In some embodiments, the capsule is additionally provided with an inner support to add tensile strength.

Any suitable method of sealing the devices may be used, including the employment of polymer adhesives and/or crimping, knotting and heat sealing. These sealing techniques are known in the art. We prefer use of a light cured methacrylate for sealing the leading end of the device. Photopolymerizable acrylic glue is commercially available, from, e.g., Ablestik Laboratories, Newark, Del.), Luxtrak Adhesives (LCM23 and LCM24), or ICI, (LCM-25). In addition, any suitable "dry" sealing method can also be used. In such methods, a substantially non-porous fitting is provided through which the cell-containing solution is introduced. Subsequent to filling, the device is sealed. Such a method is described in copending U.S. application Ser. No. 08/082,407, abandoned, herein incorporated by reference.

The methods and devices of this invention are intended for use in a mammalian host, recipient, patient, subject or individual, preferably a primate, most preferably a human.

For gene therapy, the capsular membrane is selected so that the viral vector is substantially released from the capsule, but the packaging cells are retained. Such membranes typically have moderate to high molecular weight cutoff values (MWCOs) or are microporous, and have high hydraulic permeabilities, resulting in enhanced diffusional characteristics.

The ordinarily skilled artisan can measure the viral permeability of a particular membrane to determine the rate of viral particle release for any given viral particle, using known methods. Fibers can be tested for their viral permeability using methods such as plaquing techniques that are known to be particularly sensitive to viruses. In many cases, the particular virus of interest may be tested directly by loading a given concentration of packaging cells, or virus, into the lumen of a fiber, securely sealing the ends, and placing the fiber in a bath solution. The bath solution can then be tested at desired time intervals and assayed for viruses using standard plaquing procedures (Davis, B., *Microbiology: Including Immunology and Molecular Genetics*, 3rd ed., Harper & Row (1980)).

In cases where it may be undesirable to test the virus of interest directly, a model of the virus of interest can be used. Bacteriophages of similar dimensions of the virus of interest serve as useful models due to their viral nature. A variety of phages are available from the ATCC, and are also listed in *Molecular Cloning: A Laboratory Manual* (Sambrook, J. et al., Cold Spring Harbor Laboratory Press, 1989).

Table 1 gives the sizes of some representative animal viruses. They range from 18–26 nm for the parvoviruses to 150–300 nm for the paramyxo (parainfluenza) viruses.

TABLE 1

Sizes of Representative Animal Viruses

| Virus Family | Virus | Diameter (nm) |
|---|---|---|
| Parvoviridae (DNA) | Parvo | 18–28 |
| Adenoviridso (DNA) | Adeno | 70–90 |
| Picomaviridas (RNA) | Rhino | 24–30 |
| Reoviridae (RNA) | Reo | 75 |
| Orthomyxoviridae (RNA) | Influenza | 80–120 |
| Paramyxoviridae (RNA) | Paramyxo (para influenza) | 150–300 |
| Retroviridae | oncovirus (Type C, B, D) | 100 |

Microporous membranes are preferred for constructing the capsules of this invention. Microporous membranes (and methods of making them) are known. See, e.g., Strathmann in "Production of Microporous Media by Phase Inversion Processes," *Materials Science of Synthetic Membranes*, ACS Symposium Series 269, American Chemical Society, Washington D.C. (1985).

Any suitable microporous membrane may be used for fabrication of the devices of this invention, including those disclosed in U.S. Pat. Nos. 4,968,733 and 4,976,859 herein incorporated by reference. Also suitable are the membranes referred to in U.S. Pat. No. 4,629,563, incorporated herein by reference, as well as EP 342 026, EP 356 045 and PCT 95/23598, all of which are herein incorporated by reference.

Microporous membranes typically consist of a dense plurality of interconnected pores. The pore density of microporous membranes can vary. For example, EP 342 026 refers to membranes having a pore density from 35 to 105 pores per square $\mu$m of membrane surface area. The average pore sizes of microporous membranes can vary from as small as 1 nm to as large as 10 $\mu$m. See PCT 95/02805. Further, the porosities of microporous membranes also vary. EP 356 045 refers to membranes having porosities in the range of 30 to 65 percent.

The specific pore surface area can be determined by BET analysis using a Quantasorb™ apparatus manufactured by the Quantachrome Corporation. See Brunauer, S., et al., *Journal of American Chemical Society*, 60, p. 309 (1938); and Nelson, F. M., et al., *Analytical Chemistry*, 30, p. 1387 (1958), incorporated herein by reference.

The desired rate of release of viral particles from the capsules of this invention can be achieved by choice of the appropriate jacket material. The rate of release of a selected agent through a microporous membrane depends on the fiber wall thickness, effective diffusivity, and solute distribution coefficient between lumen and the pore liquid. By careful selection of the solvent/solute/membrane system, enormous flexibility in the rate of release of a selected agent (i.e., a viral vector) can be achieved. See PCT 95/02805.

The release rate of the viral particles may also be regulated by choice of a symmetric or asymmetric membrane. Use of an asymmetric membrane can decrease the release rate, especially for relatively large agent molecules. See PCT 95/02805.

According to the devices and methods of this invention, the vector-producing packaging cells are isolated from host tissue by a physical barrier. The thickness of this physical barrier can vary, but it will always be sufficiently thick to prevent direct contact between the cells and/or substances on either side of the barrier. The thickness of this region generally ranges between 5 and 200 microns; thicknesses of 10 to 100 microns are preferred, and thicknesses of 20 to 75 microns are particularly preferred. Types of immunological attack which can be prevented or minimized by the use of the instant vehicle include attack by macrophages, neutrophils, cellular immune responses (e.g., natural killer cells and antibody-dependent T-cell-mediated cytolysis (ADCC).

For gene therapy within immunologically privileged sites, such as the brain, use of larger membrane pore sizes are possible. For implant sites other than immunoprivileged sites, it might be desirable to use capsule jackets with pore sizes approximating the size of the viral particle (but permitting passage of the viral particle therethrough). In such capsules, the packaging cells are slowly killed by means other than cell-mediated killing. This may be important where a slow decrease in the virus "dosing" is desired over time, and may help to avoid a major patient reaction by the sudden death of all the packaging cells.

The need for immunosuppression of the patient is greatly reduced or eliminated using the devices and methods of this invention. In fact, it is generally undesireable to immunosuppress the patient since the immune system may play a role in sustained cancer or tumor regression following thymidine kinase or ganciclovir treatment. See, e.g., Barba et al., *Proc. Natl. Acad. Sci. USA*, 91, pp. 4348–52 (1994). However, should immunosuppression be required, it can be achieved by use of either immunosuppressive drugs, such as cyclosporin, or local immunosuppression strategies employing locally applied immunosuppressants. Local immunosuppression methods are disclosed by Gruber, *Transplantation*, 54, pp. 1–11 (1992), and by U.S. Pat. No. 5,026,365, incorporated by reference.

The vector-producing packaging cells contemplated for encapsulated cell therapy of this invention include any suitable packaging cell that is capable of producing and releasing viral vectors comprising at least one heterologous gene encoding at least one biologically active molecule. Preferred viruses include herpes simplex virus and retroviruses.

Particularly preferred are retroviruses. Recombinant replication deficient retroviruses are conventionally made by passaging a retroviral vector with all or portions of the gag, env, and pol genes deleted through a "packaging cell line" that has been stably transfected with complementing viral protein coding genes. The sequences of the vector and the packaging sequences are designed so that only the recombinant viral genome will be packaged into new viral particles. The result is an infectious particle that cannot replicate new virus.

One widely used retroviral packaging cell line is PA317, which was made by transfecting mouse fibroblasts with the pPAM3 plasmid. WO 95/26411, pp. 44–45. ψCRIP is another commonly used, and preferred, packaging cell line. See, e.g., Tamiya et al., *Gene Therapy*, 2, pp. 531–38 (1995). Standard transfection techniques such as calcium phosphate co-precipitation, DEAE-dextran transfection or electroporation may be utilized. Commercially available mammalian transfection kits may be purchased from, e.g., Stratagene.

A number of stable producer cell lines are available for recombinant retroviruses. See, e.g., U.S. Pat. No. 5,449,614, incorporated herein by reference. In some instances, it may be possible to provide gene therapy using the transplant recipient's own cells as packaging cells (e.g., in the case of tumor, endothelial or epithelial biopsies, etc.). Cells that are syngeneic to those of the recipient may also be used. WO 95/26411 refers to methods of transforming virus-producing packaging cells from human cells.

Although the use of autologous or syngeneic cells as packaging cells is possible, their use is contra-indicated as immune killing appears to be important to the success of the retroviral therapy.

Shown below are some known packaging cell lines.

TABLE 2

Packaging Cell Lines

| Packaging cell | Type of vector packaged | Permissive host cells for vectors | | |
| --- | --- | --- | --- | --- |
| | | Rodent | Avian | Human |
| Ψ2 | MLV | + | – | – |
| ΨAM | MLV | + | + | + |
| PA12 | MLV | + | + | + |
| PA317 | MLV | + | + | + |
| Clone 32 | MLV | + | – | – |
| GP + E – 86 | MLV | + | – | – |
| ΨCRIP | MLV | + | + | + |
| ΨCRE | MLV | + | – | – |
| D17-C3 | REV, MLV | +[a] | + | +/–[b] |
| DSN | REV, MLV | +[a] | + | +/–[b] |
| DAN | REV, MLV | + | + | + |
| pHF-G | ASLV | – | + | – |
| Isolde[c] | ASLV | – | + | – |
| Q2bn/QΔdh[c] | ASLV | – | + | – |

[a]Mouse cells are infected poorly.
[b]Some primate cells are permissive for infection and expression, but not productive replication, of REV and its vectors.
[c]ASLV packaging cells are currently limited to subgroup A anv.

As Table 2 shows, not all the vectors produced by the listed packaging cells have human cells as permissive hosts. For use in treatment of human diseases or disorders, the viral vector must be capable of infecting the target tissue or cells in the human host or patient. However, an ecotropic retrovirus can be converted to an amphotropic one by, e.g, modification of the env gene expressed by the packaging cell line. See, e.g., WO 92/07943. Further, packaging cells (and the ecotropic vectors they produce) are useful in development of in vitro models and in vivo non-human models for disease treatment and prophylaxis using the gene therapy approach of this invention.

Some retroviruses, such as HIV-1 retrovirus and lentivirus, infect only post-mitotic cells. However, most retroviral vectors will only integrate and subsequently express their genes in proliferating tissue, such as cancer or tumor tissue. This feature of retroviral vectors may be particularly advantageous for the selective introduction of genes into cancers or growing tumors into largely non-mitotic tissues such as the brain. Since in this case the tumor is the predominant mitotic cell type, it is essentially the only tissue that will integrate and express the vector genes. The risk of integration into macrophage-derived cells, blood cells, and endothelial cells is minimal.

Retroviruses are also desirable in that some can be engineered for tissue-specific targetting. This tissue-specific targeting is possible where the envelope of the retrovirus carries a specific factor, one that will bind to receptors found on the cell membrane of the target cell. For example, where the factor is one that fuses to a hormone receptor, such as erythropoietin, the retrovirus will be extremely infective of cells expressing erythropoietin receptors. Tissue-specific retroviruses can be manufactured by fusing the gene for the receptor-binding factor to the gene for the retrovirus envelope protein. See, e.g., Somia et al., *Proc. Natl. Acad. Sci. USA*, 92, pp. 7570–74 (1995); Kasahara et al., *Science*, 266, pp. 1373–76 (1994).

Several retroviral vectors based on Moloney murine leukemia virus are commercially available and can be used to insert genes of interest into retroviral vectors. These vectors are typically named according to the order of genetic elements in the vector: L, long terminal repeat (LTR); N, neo; S, simian viruse 40 (SV40) early promoter, C, human cytomegalovirus (CMV) immediate early promoter; and X, cloning site. Sequences surrounding the retroviral vector were derived from pBR322 and contain the ampicillin resistance gene, allowing amplification of the vectors as plasmids in bacteria.

As discussed above, any suitable packaging cell line may be used to produce replication defective retroviral particles according to the methods and devices of this invention. Various retroviral vectors with amphotrophic host ranges are known. See, e.g., U.S. Pat. No. 5,449,614, incorporated by reference, referring to vectors carrying the adenosine deaminase (ADA) gene under the control of the human histone H4 promoter or the murine Thy-1.2 promoter.

WO 94/29437, incorporated herein by reference, also refers to useful retroviral vectors that contain a U-3-free 5' LTR, a partially deleted 3' LTR and an internal promoter recognized by a target host cell. These recombination-free vectors are designed to self-inactivate after one round of retroviral replication.

Additional retroviral vectors useful for gene therapy are provided in WO 92/07943, incorporated by reference.

In one embodiment, the gene of interest can be inserted in the HindIII site under the control of SV40 and CMV promoters in the retroviral vectors LNSX and LNCX, respectively.

Alternatively, the gene of interest can be inserted in the BamHI site under the control of LTR in LNSX. Furthermore, the internal promoters of SV40 and CMV in LSNX and LNCX, respectively, can be replaced with alternative promoters for tissue-specific expression. It is important to remove the polyadenylation signals from the inserted DNA as these will cause premature termination of transcription and reduce the levels of viral transcripts.

The gene to be delivered can be any sequence of interest that encodes a desired product. The genes encoding numerous biologically active molecules have been cloned and their nucleotide sequences published. Many of these genes are publicly available from depositories such as the American Type Culture Collection (ATCC) or various commercial sources. Genes that are not publicly available may be obtained using standard recombinant DNA methods such as PCR amplification, genomic and cDNA library screening with oligonucleotide probes. Any suitable known gene coding for a biologically active molecule may be employed in the methods of this invention.

The gene may encode a surface membrane protein, a secreted protein, a cytoplasmic protein, or there may be a plurality of genes that encode different types of products. The proteins that are expressed, singly or in combination, may involve homing, cytotoxicity, proliferation, immune response, inflammatory response, clotting or dissolving of clots, hormonal regulation, or the like. These proteins may be naturally-occurring, mutants of naturally-occurring proteins, unique sequences, or combinations thereof.

In one embodiment, a gene expressing an anti-tumor or anti-cancer agent would be desirable. Such genes would include genes encoding anti-proliferative agents, genes encoding apoptosis-inducing molecules, genes encoding tumor suppressor molecules, genes encoding toxins, anti-sense sequences, and "suicide genes" that render the infected cells sensitive to a subsequent treatment.

Suitable genes encoding antiproliferative agents include the genes encoding various cytokines having anti-proliferative action (e.g., interferons such as IFN-$\beta$, IFN-$\alpha$, IFN-$\gamma$ and interleukins such as IL-2, IL-3, IL4, IL-6, L-7, and IL-10). The genes encoding these molecules are known. See, e.g., U.S. Pat. Nos. 4,530,901, 5,376,567, 4,588,585, and 5,326,859, all of which are incorporated herein by reference. Other molecules that may be useful in the treatment of cancers or tumors include TNF-$\alpha$ and granulocyte macrophage colony stimulating factor (GMCSF).

Suitable genes encoding apoptosis inducing molecules include the genes encoding Fas ligand (FasL) and Fas receptor (Apo-1) as provided in EP 675 200 and WO 95/32627, as well as the genes encoding lymphotoxin, CD40L, and TNF-$\alpha$. Suitable tumor suppressor genes include p53.

Suitable genes for encoding bacterial toxins include the genes encoding as diphtheria toxin, cholera toxin, Shigella toxin, or pseudomonas exotoxin A. Other suitable toxins include genes encoding molecules that render cells sensitive (or more sensitive) to chemotherapy drugs. For example, the gene encoding CYP2B1 may be delivered to cancer or tumor cells to render them sensitive to oxazaphosphorine anticancer drugs. See, e.g., Chen and Waxman, *Cancer Research*, 55, pp. 581–89 (1995). Antisense sequences that may be useful in oncology applications may reduce tumor growth by inhibiting translation of oncogenes such as the myc gene or the ras gene. Further, the gene encoding Flk-1 or the VEGF receptor may also be useful.

Suitable "suicide genes" include HSV-TK or CodA, would yield tumor cell death upon treatment with ganciclovir (or related nucleoside analogs including acyclovir and FIAU) or 5-fluorocytosine, respectively.

The foregoing genes may be useful in the methods and devices of this invention in the treatment of cancers and tumors, including primary and secondary tumors of the brain, lung, thymus, pleura, liver, pancreas, kidney, gut, peritoneum, ovary, uterus, prostrate, or other target tissue site.

The techniques and devices of this invention may be applicable to lysis of numerous types of dividing cells. In addition to treatment of tumors or cancers, undesired cell division, such as vascular smooth muscle cells creating neointimal hyperplasia at the site of the distal anastomosis of an artificial arterial bypass (atherosclerosis), may also be treated using the devices and methods of this invention.

Similarly, treatment of undesired neovascularization in disease states including macular degeneration may also be treated using the methods and devices of this invention. Further, the devices and methods of this invention may also be used in the reduction of thrombogenicity after vascular surgical procedures. The genes useful for such angiology applications include the foregoing genes, as well as tissue plasminogen activator (tPA), single chain urokinase plasminogen activator, parathyroid hormone, and prostoglandin H synthetase.

Metabolism disorders may also be treated using the devices and methods of this invention. The genes encoding glucocerebrosidase, uroporphyrinogen synthase, Factor VIII, Factor IX, and the receptor for low-density lipoprotein may be useful in the treatment of indications such as Gaucher's disease, genetic and acquired disease of the liver (including Factor VIII or Factor IX deficiency, or α1-antitrypsin deficiency), hypercholesterolemia, and porphyria.

Similarly, various hematology and immunology indications, including severe combined immune deficiency (i.e., adenosine deaminase deficiency, X-linked SCID, and CD3-γ deficiency), haemophilia, thalassemia, sickle cell anemia, paroxysmal nocturnal hemoglobinuria and pyruvate kinase deficiency may be treated by providing the genes encoding, e.g., Factor IX, adenosine deaminase, β-globin, erythropoetin, and pyruvate kinase.

Other suitable genes include anti-apoptotic genes, e.g., Bcl-2 and Bcl-2-like genes, to prevent unwanted death of certain cell populations. Where the target cells are post-mitotic, delivery of a retroviral vector capable of infecting post-mitotic cells is required. Such treatment, for example, could enhance the survival of dopaminergic neurons in patients suffering from Parkinson's disease, Huntington's disease, or Alzheimer's disease. Delivery of NOS could be used to detoxify free radicals that kill cells.

The delivered gene may encode an antisense sequence that modulates a particular pathway by inhibiting a transcriptional regulation protein, or turns on a particular pathway by inhibiting an inhibitor of the pathway. For example, an antisense sequence could combat Alzheimer's disease by inhibiting production of the β-amyloid precursor or tau proteins associated with that disease.

The gene to be delivered could contain enhancer binding sequences to increase the likelihood of transcription of the delivered gene and to draw the cell's transcription factors away from endogenous cell DNA. Enhancer binding sequences for the leptin promoter or the leptin receptor promoter, for example, could be used to control obesity.

Also useful would be genes coding for neurotransmitter-synthesizing enzymes. Genes expressing enzymes such as tyrosine hydroxylase or L-dopa decarboxylase could be used to treat patients suffering from Parkinson's disease or pain, by facilitating the catecholamine biosynthesis. The gene encoding glutamic acid decarboxylase could be used to control epilepsy. Delivery of the gene for choline acetyltransferase could be used to combat Alzheimer's disease.

The gene could encode a growth factor, trophic factor, enzyme, or hormone, such as NGF, GDNF, CNTF, NT4/5, CT-1, OP-related factors or obesity-related factors. The gene may also encode any other biologically activer molecule.

Any suitable promoter may be used as the internal promoter in the retroviral vector. Such promoters include direct expression from the retroviral LTR, or heterologous promoters including the thymidine kinase promoter of herpes simplex virus, the early promoter of SV40, the immediate early promoter of human cytomegalovirus, the β-actin promoter, the β-globin promoter, the glial fibrillary acidic protein (GFAP) promoter and the myelin basic protein (MBP).

The retroviral vector may be engineered to insert the desired heterologous gene and promoter sequences according to standard techniques, as set forth in, e.g., U.S. Pat. No. 5,449,614.

In one embodiment, the gene therapy described herein is contemplated as a potential treatment for glioblastomas. Glioblastomas are the most common form of malignant primary brain tumor and the third leading cause of death from cancer for people 15–34 years of age. Little progress has been made in glioblastoma treatment. Conventional treatment consists of surgery to remove the bulk of the tumor followed by irradiation to ablate the remaining cancerous cells. Other approaches include chemotherapy and conventional gene therapy. Prognosis is poor. Median survival for patients with diagnosed glioblastoma is approximately nine to twelve months after diagnosis, with a five-year survival rate at only 5%.

The present invention allows for the treatment of glioblastomas and other brain tumors by implantation of encapsulated packaging cells near the tumor site or the cavity left after resection. The packaging cells carry a retroviral vector containing the gene for the enzyme herpes simplex virus thymidine kinase ("HSV-tk"). Such packaging cell lines are known. See, e.g., Ram et al., *J. Neurosurg.*, 81, pp. 256–60 (1994), referring to the amphotrophic retroviral producer cell line PAT 2.4, derived from NIH3T3 cells. See also Culver et al., *Science*, 256, pp. 1550–52 (1992). Dividing cells are transduced by the retroviral vector, and those cells expressing the gene become susceptible to the antiviral drug ganciclovir. Approximately 7 days after transplantation of devices containing packaging cells into the brain, the patient is treated with ganciclovir. Ganciclovir is specifically converted by HSV-tk to intermediates capable of inhibiting DNA synthesis by the cell, resulting in cell death. Accordingly, both the packaging cells (which also express HSVtk) and the infected tumor cells expressing HSVtk are killed by the drug. Ram et al. *Cancer Research* 53: 83–88 (1993).

Culver et al., *Human Gene Therapy*, 5, pp. 343–379 (1994) refers to therapy for killing malignant cells while sparing healthy ones consisting of a two step injection process a week apart. The injections are directly into the cranial tumor bed via a hole drilled in the skull. In the first step up to $10^9$ recombinant mouse fibroblast cells transformed by an emasculated retrovirus packing a herpes simplex virus gene encoding thymidine kinase (HSVtk) are injected into the patient's brain. See also Oldfield et al., *Human Gene Therapy*, 4, pp. 39–69 (1993).

One week later, the anti-viral drug ganciclovir is administered. Those host cells genetically transduced with the tk gene (and that express it) are susceptible to ganciclovir. Because the retroviral particles infect dividing cells only, the glioma cells are preferentially targeted. In addition, the ganciclovir "kills" the packaging cells, which also express the tk gene.

The packaging cells act as a slow-release system for approximately seven days, producing viral particles containing a heterologous DNA encoding the HSVtk gene that the vector transfers to the target tumor cell. Further, the retroviral vector has been engineered so that it cannot replicate in situ after delivering its DNA sequence.

But some difficulties arise from this suicide gene transfer technique. To date the major deficiency is short viral-particle life span, which limits the efficacy of this treatment and its application in a human phase I protocol.

Another potential problem with the unencapsulated gene therapy approach in immunosuppressed patients (or in patients whose immune system does not recognise the packaging cells as "foreign") is that packaging cells may fail to express the HSVtk gene, making them refractory to the ganciclovir treatment, allowing the possibility that the packaging cells may divide unchecked and produce tumors.

In earlier rodent experiments, a packaging line releasing HSV-tk retroviral vectors was co-grafted (unencapsulated) with a syngeneic 9L gliosarcoma tumor and resulted in an inhibition of tumor growth. However the period of gene delivery was curtailed by immune rejection of the vector producing line within 3 to 4 days after injection. In such conditions, efficient vector production and release might not exceed 24 h.

The methods and devices of this invention allow prolonged in vivo release of viral particles compared to direct grafting of packaging lines within a tumor mass. Implantation of such a capsule with a glioma, associated with the "bystander effect" may achieve the transduction of HSV-tk gene to a major part of the tumor cells that are sensitized to a ganciclovir treatment. See, e.g., Wu et al., *Neurosurgery*, 35, pp. 1094–1103 (1994).

Further, the methods and devices of this invention permit extension, where desirable, of retroviral delivery even during the administration of ganciclovir to the patient. This is because encapsulation may directly or indirectly protect the packaging cell line from the ganciclovir (in the case of transduction of HSVtk). Ganciclovir appears to preferentially kill fast-dividing cells expressing HSVtk. The encapsulation will retard division of the packaging cells and as such may provide protection to the cells, at least for a time. The core matrix may also serve to protect the packaging cells from ganciclovir-induced death. Alternatively, the packaging cell lines may be inhibited in their mitotic activity using mitotic inhibitors or irradiation, possibly affording protection to the cells. This allows the treatment of patients immediately with ganciclovir and treatment for long periods post-implantation. Extension of the therapy period even during administration of ganciclovir could also be accomplished by use of a conditionally-immortalized packaging cell lines, in which the cells are not ganciclovir-sensitive (cells must undergo DNA synthesis to be sensitive to ganciclovir). Safety would not be compromised, since the capsule could be retreived.

Accordingly the methods and devices of this invention permit encapsulated cells to continue to release retrovirus while ganciclovir is being administered. This would most likely increase the number of cells that are killed by the therapy.

It may be desirable to transduce cells with multiple genes to achieve the optimum gene therapy protocol. The devices and methods of this invention permit delivery of several viral vectors simultaneously by encapsulating packaging cells that release different viral vectors engineered with different genes. In addition, the number of devices implanted as well as the number of cells and therefore the number of viral particles released from each device, can be varied, thus permitting regulation of the relative amounts of viral particles delivered.

In another embodiment, the encapsulated gene therapy approach of this invention is used to deliver viral particles containing the gene encoding granulocyte macrophage colony stimulating factor (GMCSF). GMCSF is a potent enhancer of immune function and targets cells, including tumor cells, for direct cell killing. GMCSF is a particularly preferred candidate for delivery using the encapsulated gene therapy approach of this invention. This is because according to this embodiment, the packaging cells remain alive during the course of treatment. Cell-to-cell contact is required for killing the encapsulated cells—thus the cells in the capsule continue to survive, unaffected by the gene they package and express. In the event that the cells escape, they become targetted for destruction. This provides a convenient way to continue to provide retroviral particles throughout the therapy. Use of conditionally-immortalized human cells may be particularly appropriate for this embodiment. Such cells could be rendered non-mitotic for encapsulation—this would permit use of very "open" or permeable membranes without any immune problems, yet allowing larger numbers of viral particles to exit the device. The packaging cells would be targetted for destruction if they escaped the device.

The cell-loaded devices will be tested for release of retrovirus in vitro and implanted near or within the target patient tissue using known techniques. For implantation in the brain, known imaging and stereotaxic equipment can be used. The surgical tools and techniques for implanting the capsules of this invention are known. See, e.g., PCT 92/05369 and PCT 93/12353, and U.S. Pat. No. 5,487,739, incorporated herein by reference.

It may be necessary to vary the dosage of retroviral particles delivered to the patient. This can be accomplished by appropriate choice of a packaging cell that produce a greater or lesser retroviral vector titer, as desired. Further, device volume and packaging cell loading density may be easily varied over at least three orders of magnitude. In addition, delivery of retroviral particles can be varied by implanting more than one capsule, depending on the therapy contemplated. Any number of capsules can be implanted, although certain for certain implant sites, particularly in the CNS, we prefer between 1–10 capsules.

The capsule containing the packaging cells will be left in place as long as necessary for a given therapy. Depending on the gene being transduced, the devices containing the packaging cells will be implanted for varying amounts of time. Therapies using some genes may require extended periods of time in vivo.

In order that the invention described herein may be more fully understood, the following examples are set forth. It should be understood that these examples are for illustrative purposes only and are not to be construed as limiting the scope of the invention in any manner.

EXAMPLES

Example 1

Preparation of Macrocapsules

Microporous fibers were prepared by extruding a 10% polyethylene oxide (MW=100K), 10% PAN/PVC (MW=100K), 80% dimethyl formamide (w/w) solution through the outer lumen of a coaxial extrusion nozzle. Water was used as a coagulant and was coextruded with the polymer through the center bore of the nozzle. The procedure is essentially as described in U.S. Pat. No. 5,158,881, herein incorporated by reference. Nominal MWCO of these fibers was 2,000 kD. The fiber had an inner diameter of 0.8 mm and an outer diameter of 1 mm.

Example 2

Infection of BHK Cells Using Encapsulated Packaging Cell Line Producing a Retroviral Vector A VIK packaging line was encapsulated in a hollow fiber capsule having a jacket comprising a microporous membrane. VIK cells produce replication-defective particles that pass through the microporous membrane.

The continuous delivery of viral particles from encapsulated VIK cells yielded in vitro infection rates of dividing BHK target cells of 10 to 100 fold higher than those obtained in standard retroviral infection methods.

Retroviral vector

The VIK packaging cells used in this study release an ecotropic retroviral vector containing the herpes simplex virus-tk ("HSV-tk") type 1 gene. The packaging cell line was kindly provided by X. O. Breakfield (Molecular Genetics Unit, Mass General, Boston). The 2.8 kb HSV-tk fragment, obtained from plasmid pBRTK, was cloned into the BamHI site of plasmid pLRNL—the resulting plasmid was designated pLTKRNL. An ecotropic packaging cell line, ψ2 was transfected with pLTKRNL to produce the recombinant VIK retrovirus. See, e.g., Ezzeddine et al., *New Biologist*, 3, pp. 608–6124 (1991).

The infected target cells express the HSV-tk gene, rendering them sensitive to nucleoside analogs such as ganciclovir or acyclovir. Chiocca et al., *Gene Therapeutics*, pp. 245–262 (1995). Once these analogs are incorporated into the dividing cell genome, DNA strand breaks occur, leading to the death of the target cells. Ezzeddine et al., *New Biologist*, 3, pp. 608–14 (1991). The retroviral vector genome also contains the neomycin resistance (Neo-R) gene, conferring resistance to aminoglycoside analogs such as G418 to the cells expressing the gene. G418 therefore is used to select out the non-expressing cells. The HSV-tk gene was under control of MoMuLv LTR promoter and the NeoR gene was under control of RSV promoter as described by Ezzeddine et al., supra.

Production of retroviral vectors

Replication defective HSV-tk bearing retroviral vectors were produced by the ecotropic retrovirus packaging line VIK. VIK cells were cultured in Dulbecco's modified Eagle medium (DMEM) (GIBCO) supplemented with 10% fetal calf serum (FCS), 1% L-glutamine and 1% Penicillin/Streptomycin (P/S). These cells were selected and maintained under 1 mg/ml G418 selection. Control baby hamster kidney cells (BHK) were cultured in the same conditions without the G418 selection and were used as target cells.

Determination of the viral titre

BHK target cells were exposed to medium harvested from a 75 cm$^2$ flask of VIK cells. The medium was filtered through a 0.22 μm filter. On the day of infection, the medium is removed from the target cells and medium containing virus is added to stocks with dilutions that differ by 10-fold. The transformants expressing the neomycin resistance gene were selected under 1 mg/ml G418 for 10 days. The colonies formed by the surviving cells were counted and the titer (CFU) was calculated in the following way:

$$CFU = \frac{\text{colony no.}}{\text{Virus vol (ml)} \times \text{replication factor}}$$

The vector titer obtained following a 10-day G418 selection period was 4.75×10$^5$ CFU. This titer is similar to that previously published by Ezzeddine for the VIK packaging line.

Encapsulation of the VIK packaging line

About 6.5×10$^6$ VIK cells harvested from confluent flasks were suspended into 375 μl PC-1 medium and then mixed with 375 μl of a collagen matrix (Zyderm™). Aliquots of the resulting cell suspension (approximately 5×10$^6$ cells/μl) was gently injected in microporous fibers substantially similar to those described in Example 1 (Akzo, polyether sulfone TF 10/10 microporous hollow fiber membranes). Typically the fibers were loaded at a density of 75,000 cells per 0.9 μl. The fibers had an ID of about 480 μm, an OD of about 600 μm, a break point of about 45 g, hydraulic permeability of 142 ml/m$^2$/min/mmHg and a volume of about 1.8 μl. We used small volume fibers in these studies, however, larger volume capsules are preferred for human studies.

The fibers were closed by heat sealing both ends with the help of heated forceps. Each capsule was 4.5 cm long. These capsules were maintained in DMEM without G418 selection. Although heat sealing is satisfactory, we prefer light cured glue seals, or dry "hub" seals, as described supra, for use in human patients.

Co-culture experiment

About 2×10$^4$ BHK cells were plated into 6-well flasks. These cells were exposed to three types of treatment.

The first group of target BHK cells was cultured with 22 μm-filtered medium harvested from a confluent VIK cell culture (as described above) for 48 hours.

The second group of target BHK cells was cultured in 1.5 ml of medium harvested from a dish containing 2 VIK capsules which had been cultured in DMEM (as described above) for 48 h.

The third group of BHK cells was co-cultured with in 4-cm-large wells, each containing a single VIK-capsule. The VIK-capsules and BHK cells were co-cultured for three time periods: 24, 48 and 96 h. The larger size of the capsules compared to the well diameter allowed us to apply the devices on the well wall, avoiding mechanical damage to the target cells laying within the well. At the end of each co-culture period, the capsules were withdrawn and fixed with 4% paraformaldehyde for histological examination.

48 h after exposure to the above treatments, BHK cells were exposed to a 1 mg/ml G418 selection for 7 days in order to select for transformants. At the end of the selection period, BHK cells were dissociated with GIBCO dissociation medium, counted on a Björk cell counter and finally exposed to 100 μM ganciclovir (Cytovene® Syntex) for 6 more days.

Co-culture experiment

Exposure to the different treatments yielded very different results. About 2×10$^4$ BHK cells survived exposure to G418 after exposure to naked VIK packaging cells. Less than 5×10$^5$ BHK cells survived G418 selection when exposed to supernatant from encapsulated VIK cells. In contrast, up to 2×10$^6$ BHK cells survived G418 selection after co-culture with encapsulated VIK cells.

This study shows that continuous release of retroviral particles using encapsulated cells leads to a much greater infection rate of dividing target cells compared to direct administration of vector particles to a target cell culture.

Co-culture duration was also important in this study. About 1–4×10$^4$ BHK cells survived G418 selection after a 24 h co-culture with encapsulated VIK cells. About 1–4×10$^5$ BHK cells survived the same selection conditions with a 48 h co-culture. In contrast, up to 1–3×10$^6$ BHK cells survived G418 selection after a 72 h co-culture.

Further, this study indicates that the infection rate of BHK target cells increased with increasing co-culture duration using encapsulated VIK cells. One explanation is that during a 72 h co-culture, the majority of the target cells go through an S phase, which is not the case in a 24 h co-culture.

Example 3

Delivery of Retroviral Particles from an Encapsulated Packaging Cell Line In Vitro 2×10$^4$ C6 or 9L cells were co-cultured with either (1) psi-VIK cell supernatant, (2) encapsulated psi2-VIK supernatant, or (3) a capsule containing containing VIK cell loaded at a density of 75,000 cells per 0.9 μl, substantially as described in Example 2. C6 tumor cells were obtained from ATCC, and cultured in Ham's F10 medium containing 15% horse serum, 5% fetal bovine serum, 1% L-glutamine, 1% penicillin/streptomycin. 9L cells were cultured in DMEM with 10% fetal bovine serum, 1% L-glutamine, 1% penicillin/streptomycin. The coculture duration was 24 h. One day following removal of the treatment, the tumor cells were exposed to G418 (1 mg/ml) for seven days, and the surviving cells counted.

Example 4

Delivery of Retroviral Particles from an Encapsulated Packaging Cell Line In Vivo The aim of this study was to demonstrate production of retroviral particles in vivo from an encapsulated packaging cell line (VIK—as described above) to infect intracerebral glial tumor cells.

On day 0, 30 Wistar rats were subjected to stereotaxic injection of $4 \times 10^4$ C6 glial cells in the right striatum. For innoculation with the C6 cells, rats were anesthetized using i.p. pentobarbitol 55 mg/kg, and placed in a stereotaxic apparatus (Kopf Instruments, Tujunga, Calif.), after the head was shaved and disinfected with iodine solution. A midline scalp incision was made and the stereotaxic guide used to mark a point 0.2 mm rostral and 3.2 mm lateral to the bregma. The skull was burred and the dura mater perforated with a needle. The depth of injection for all treatments was 5.5 mm.

Ten days following innoculation, the rats were divided into five groups of six animals each. Each group received a stereotaxic inoculation or implant with a different therapeutic agent.

Group 1 The first group of rats received a capsule consisting of a microporous membrane loaded with $1 \times 10^5$ psi2-VIK cells. The capsules were 0.8 cm long and were prepared as described in Example 2.

Group 2 The second group of rats received an empty microporous membrane with a length of 0.8 cm.

Group 3 The third group received 50 μl of DMEM containing $5 \times 10^6$ non-encapsulated psi2-VIK cells.

Group 4 The fourth group received 50 μl of the supernatant from psi2-VIK cells.

Group 5 The fifth group received 50 μl of DMEM.

On day 17, the capsules were retrieved from the first two groups of rats. All five groups were then treated with 15 mg/kg ganciclovir, beginning on day 17 and continuing until day 31. On day 32, all the animals were sacrificed and subjected to histological examination of the tumor and brain and volumetric analysis of the tumor and vector titre (CFU).

A second experiment was performed involving 18 rats and following the procedure described above for the first three groups of rats.

Figure 1:
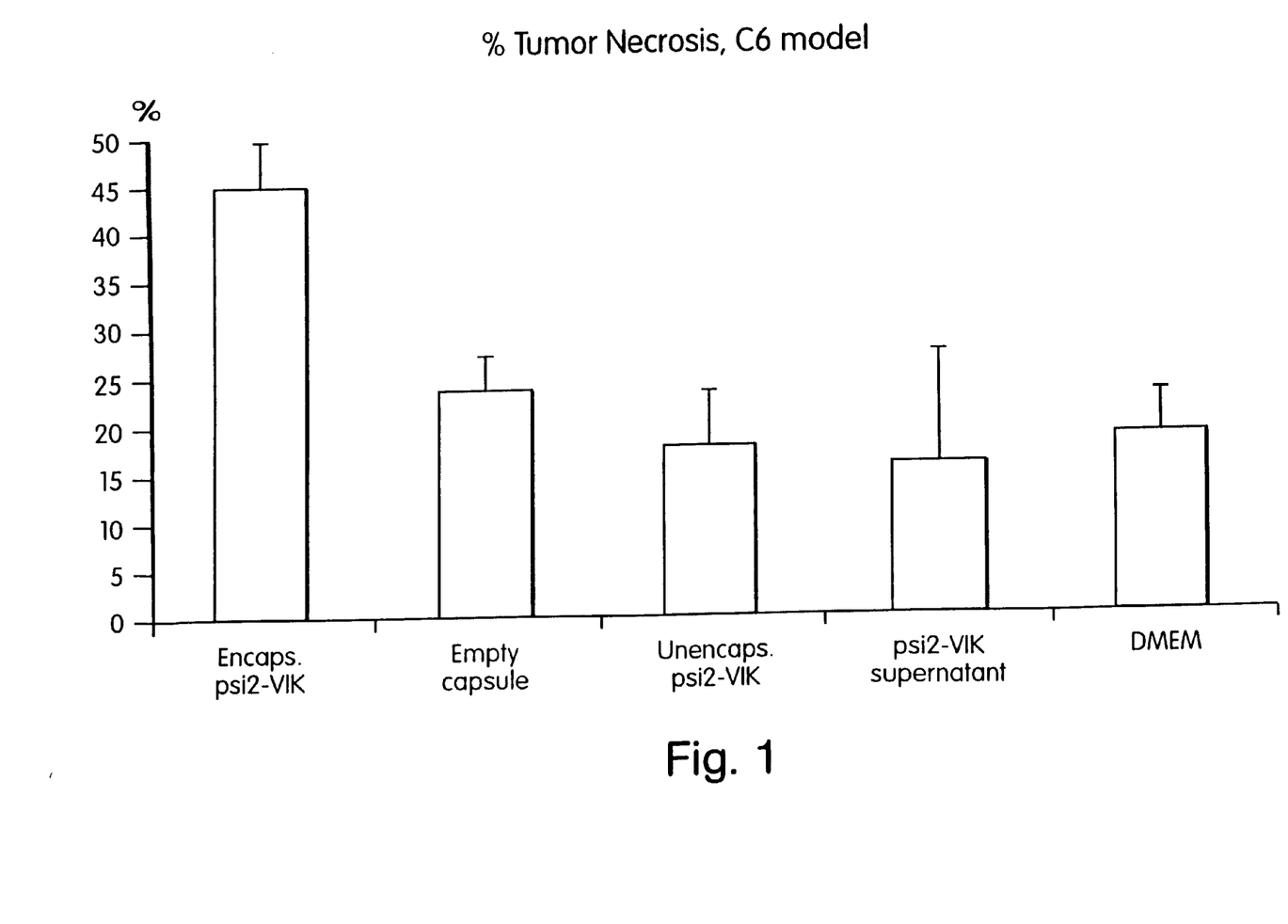
FIG. 1 shows the influence of different treatment conditions on percent necrosis in a C6 tumor model in rodent brain. The treatments were as follows: encapsulated VIK packaging cells; empty capsules; unencapsulated VIK packaging cells; supernatant from VIK cells; and DMEM medium.

The inoculation of encapsulated psi2-VIK cells resulted in significantly more retroviral infection and necrosis of glial cells than any of the other four treatments. FIG. 1 shows the percent necrosis acheived using encapsulated packaging cells to deliver the retroviral particles, compared to unencapsulated packaging cells, or supernatant containing the viral particles.

Combining the results of both experiments, the animals that received encapsulated psi2-VIK cells exhibited a mean of 44.63% necrosis of glial cells. In contrast, the animals inoculated with empty capsules, non-encapsulated psi2-VIK cells, supernatant from psi2-VIK cells, and DMEM displayed averages of 23.58%, 13.85%, 15.91%, and 18.96% tumor necrosis, respectively. Table 3 lists the mean percentage of necrosis, standard deviation and standard error for each of the five treatments.

TABLE 3

Necrosis Percentage

|  | Count* | Mean | Std. Deviation | Std. Error |
|---|---|---|---|---|
| Encapsulated psi2-VIK | 10 | 44.632 | 15.211 | 4.810 |
| Non-encapsulated psi2-VIK | 9 | 13.846 | 15.519 | 5.173 |
| Empty capsule | 10 | 23.579 | 10.647 | 3.367 |
| psi2-VIK supernatant | 3 | 15.912 | 20.074 | 11.590 |
| DMEM | 5 | 18.694 | 9.146 | 4.090 |

*Results were not available for 11 rats that died immediately following anaesthesia.

Statistical analysis was used to compare the amount of tumor necrosis observed following treatment with encapsulated psi2-VIK cells as compared to the other four treatments. The Fisher's, Bonferroni/Dunn and Scheffe tests yielded highly significant statistical differences for almost all of the comparisons. Table 4 provides the P values and confidence levels calculated using these three statistical tests.

TABLE 4

Statistical Analysis of Experiment Results

| Treatments Compared | Fisher's Test P value | Bonferroni/ Dunn Test Confidence Level | Scheffe Test P value | Confidence Level | P value | Confidence Level |
|---|---|---|---|---|---|---|
| Encapsulated psi2-VIK v. non-encapsulated psi2-VIK | <.0001 | 99.99% | <.0001 | 99.99% | .0012 | 99.88% |
| Encapsulated psi2-VIK v. empty capsules | .0019 | 99.81% | .0019 | 99.81% | .0385 | 96.15% |
| Encapsulated psi2-VIK v. psi2-VIK supernatant | .0036 | 99.64% | .0036 | 99.64% | .0646 | 93.54% |
| Encapsulated psi2-VIK v. DMEM | .0019 | 99.81% | .0019 | 99.81% | .0398 | 96.02% |

The current study shows that continuous delivery of retroviral particles in vivo by an encapsulated packaging cell line can greatly increase the infection rate of dividing target cells. Here, the introduction of encapsulated packaging cells yielded a level of infection in dividing glial cells almost double those obtained through standard retroviral infection methods, such as injection of unencapsulated packaging cells.

A third experiment was performed using 9L cells as the tumor model rather than C6 cells. The experimental design was the same, with the exception that Fisher rats were innoculated with $1\times10^4$ 9L cells. The treatments (described above) were initiated 7 days following innoculation with the 9L cells.

Example 5

Construction of a bcl-2 Retroviral Vector

One specific retroviral vector contemplated is a bcl-2 retroviral vector. The bcl-2 cDNA can be generated by reverse transcription-polymerase chain reaction (RT-PCR) of human, rat, or mouse thymus total RNA using oligonucleotide #1 (5'-TTT AAG CTT CGC CAC CAT GCC GCA CGC TGG GAG-3') (SEQ ID NO 1) AND #2 (5'-TTT AAG CTT TCA CTT GTG GCT CAG ATA GGC-3') (SEQ ID NO 2). Both oligonucleotides #1 and #2 contain the synthetic HindIII enzyme sites at the 5' end as underlined above; they facilitate the cloning of the bcl-2 RT-PCR DNA fragment into the LNSX and LNCX retroviral vectors. In addition, oligonucleotide #1 contains the concensus ribosome binding sequence CGC CAC C (Kozak sequence; double underlined above) which enhances translation efficiency of bcl-2.

Total RNA is extracted by the acid/phenol method described by Chomcyznski and Sacchi, *Anal. Biochem.*, 162, pp. 156–59 (1987). RT-PCR is performed as described by Gandelman et al., *J. Neurochem.*, 56, pp. 1024–29 (1990). Briefly, 0.5 micrograms of total RNA is reverse transcribed to generate cDNA in a 20 microliter reaction mixture according to Krug and Berger, *Meth. Enzymol.*, 152, pp. 316–25 (1987).

One to five microliters of each reaction mixture is added to make a final 50 microliter PCR mixture containing 10 pmol of each of oligonucleotide #1 and #2.

Figure 2:
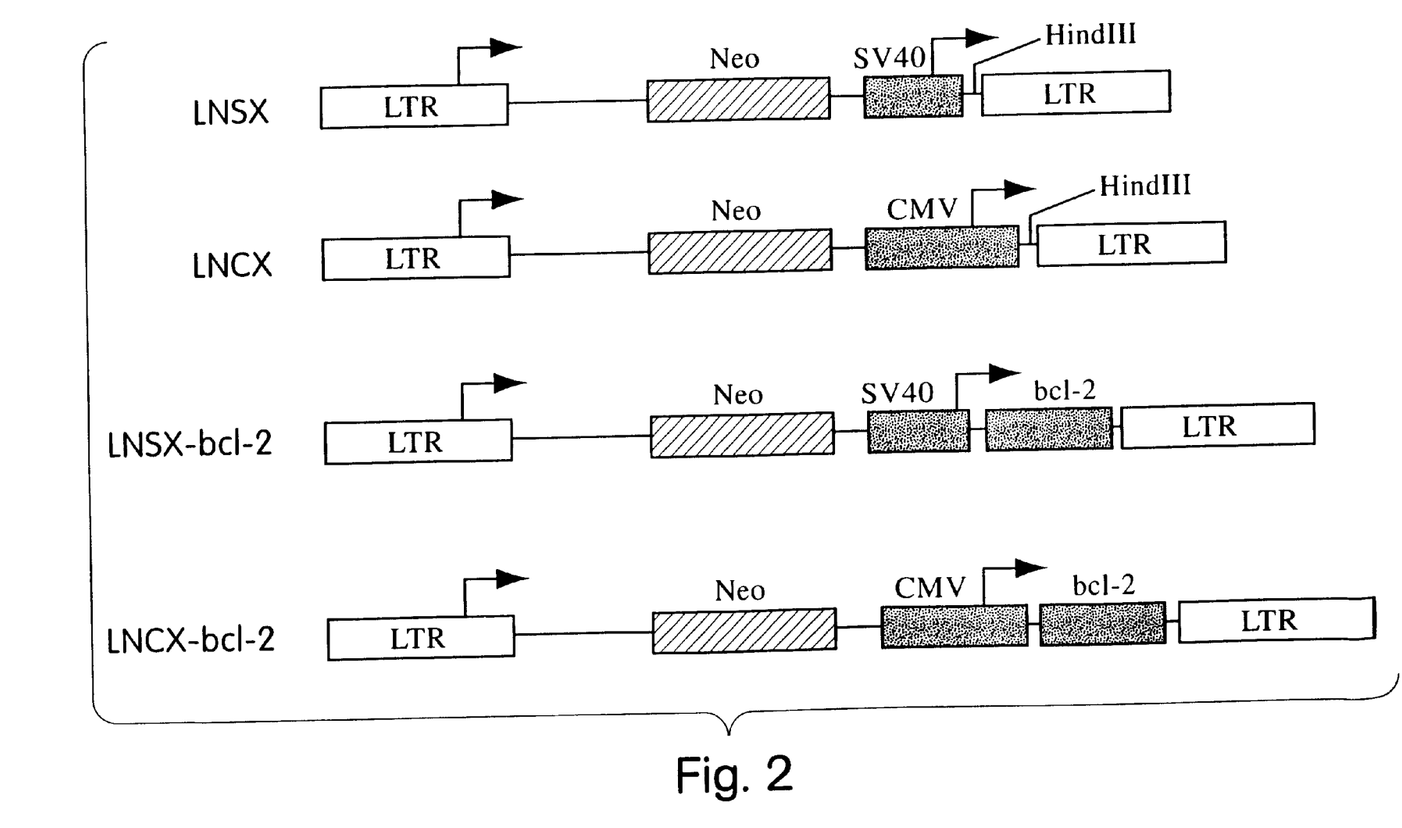
FIG. 2 depicts the retroviral vectors LNSX, LNCX, and LNSX-bcl-2 and LNCX-bcl-2. The construction of these vectors is described in example 5.

Reaction mixtures are subjected to 30 cycles of PCR. Each cycle consists of denaturation at 94° C. for 1 min, annealing at 50° C. for 1 min, and extension at 72° C. for 1 min. The PCR fragment is purified away from the used deoxynucleotides and salt in PCR reaction mixtures by the Wizard™ PCR purification kit (Promega, Madison, Wis.) according to the manufacturer's protocol. The purified RT-PCR fragment is digested by HindIII and subsequently ligated into LNXS and LNCX that have been HindIII digested and dephosphorylated by alkaline phosphatase. The ligation mixtures are transformed into DH5α bacteria and ampicillin resistant colonies are screened for positive clones. The plasmid DNA obtained from the ampicillin resistant colonies are digested by appropriate restriction endonucleases to determine insert orientation. The retroviral vectors LNSX-bcl-2 and LNCX-bcl-2 are shown in FIG. 2.

Example 6

Delivery of Retroviral Particles Using an Amphotropic Packaging Cell Line

The amphotropic packagibg cell line CRIP-MFG-LacZ was kindly provided by Dr. X. O. Breakefield (Mass General, Boston). This packaging cell line is described in Tamiya et al., *Gene Therapy*, 2, pp. 531–538 (1995). The cells produce retroviral vectors bearing the LacZ gene at a titer equivalent to $4\times10^5$ cfu/ml. The cells were cultured in the presence of 10% calf serum (GIBCO BRL, Gaithersburg, Md.), 1% penicillin/streptomycin (GIBCO), and 1% L-glutamine (GIBCO).

When used for in vivo gene transfer, the culture medium of a 75 cm² flask containing confluent CRIP-MFG cells was removed. The cells were rinsed with HBSS and incubated for 5 min at 37° C. in cell dissociation medium (GIBCO). The cells were then collected in DMEM, centrifuged at at 1000 rpm for 5 min, washed twice, and then resuspended at $2\times10^6$ cells/25 µl.

The membranes used for encapsulation were PES AKZO TF 10/10, as described in Example 1. The hollow fibers were rinsed with saline, and then loaded with CRIP-MFG cells in a suspension of collagen matrix (Zyplast, Collagen Corp., Palo Alto, Calif.) and DMEM (in a 1:1 ratio). The cell concentration was 75,000 in 0.9 µl.

In Vitro C6 or 9L and CRIP-MFG Co-culture Experiments

Rat C6 or 9L glioma cells were plated at a density of $1\times10^5$ cells per 6 cm dish (Corning Glass Works, Corning, N.Y.). 24 h after plating, cells were incubated with 5 ml of supernatant harvested from CRIP-MFG-LacZ and filtered through 0.45 µm pores (Millipore, Molsheim, France). Infections were carried out for 4 h. The cells were then washed twice with Hank's buffered saline solution (HBSS) and reincubated in DMEM/FCS/L-glut/PS. After 48 h, the cells were washed twice with HBSS and fixed with 0.5% glutaraldehyde for 10 min. The cells were then incubated at 37° C. for 24 h in a solution containing 35 mM potassium ferricyanide, 2 mM magnesium chloride, 0.01% sodium deoxycholate, 0.02% NP40, 0.2% 5-bromo-4-chloro-3-indolyl-β-D-galactosidase (Histomark).

In Vivo Experiments

Wistar rats (C6 tumor model) or Fisher rats (9L model) are innoculated with C6 or 9L cells as described above. The rats are divided into 5 treatment groups, as described above for Example 4. Upon termination of the experiment, rats are sacrificed for histological examination of the tumor and brain, and for volumetric analysis of the tumor.

Example 7

Human Clinical Trial

A membrane-based implant, containing amphotropic packaging cells producing retroviral particles encoding HSV-tk, is implanted into the tumor bed in the CNS of a patient with glioblastoma. We also contemplate that in some patients, initial surgery will be performed to remove as much of the tumor as possible prior to implantation with the encapsulated packaging cell line.

Protocol

Patient recruitment may be based on the following criteria:

a) Entry criteria:

(1) A diagnosis of high grade glioma (WHO III and IV), manifested clinically by elevated intracranial pressure and focal signs such as epilepsy or paresis of limbs and cranial nerves and confirmed by CT and/or MRI findings.

b) Exclusion criteria (1) Patient with a life threatening illness (eg, cancer, leukemia) in addition to glioblastoma; (2) Pregnant woman or woman of child-bearing potential without adequate contraception; (3) Patient with neurological involvement outside the voluntary motor system; (4) Evidence of primary disease that could cause neurologic deficit (in particular, cervical spondylosis or plasma cell dyscrasia); (5) Patient participating in any concurrent investigation drug trial.
Implantation:

Patients receive a hollow fiber implant or a round implant (e.g., shaped as a disk) containing packaging cells that produce retroviral particles encoding HSV-tk. A suitable surgical procedure, such as that described in U.S. Pat. No. 5,487,739, incorporated herein by reference, may be used to implant the devices of this invention.

retroviral vectors of 100 nm diameter thereacross, permitting release of said viral vector from said capsule.

2. The capsule of claim 1 wherein the core additionally comprises a matrix, the packaging cells being immobilized by the matrix.

3. The capsule of claim 1 wherein the jacket comprises a hydrogel or thermoplastic material.

4. The capsule of claim 1 wherein the gene encodes a biologically active molecule selected from the group consisting of anti-proliferative agents, apoptosis-inducing molecules, bacterial toxins, tumor suppressor molecules, and anti-apoptotic molecules.

We claim:

1. A biocompatible capsule comprising:
   a core comprising living packaging cells that secrete a viral vector for infection of a target cell, wherein the viral vector is a retroviral vector, the vector comprising a heterologous gene encoding a biologically active molecule operably linked to a promoter that regulates expression of the biologically active molecule in the target cell, the heterologous gene being no more than 8 kb in length; and
   an external jacket surrounding said core, said jacket comprising a permeable biocompatible material, said material having a porosity selected to permit passage of retroviral vectors of 100 nm diameter thereacross, permitting release of said viral vector from said capsule.

5. The capsule of claim 1 wherein the packaging cells are conditionally immortalized.

6. A method for making a biocompatible capsule for delivery of a viral vector, comprising the steps of:
   selecting a jacket, the jacket comprising a biocompatible material having a porosity selected to permit passage of retroviral vectors of 100 nm diameter thereacross, permitting release of the retroviral vector,
   loading packaging cells into the jacket, the packaging cells secreting said viral vector comprising a heterologous gene encoding at least one biologically active molecule operably linked to a promoter that regulates expression of the biologically active molecule in the target cell and being no more than 8 kb in length; and sealing the jacket to encapsulate the packaging cells.

7. A method of delivering a viral vector to a cell in vitro by placing at least one capsule in proximity with the cell, said capsule comprising:

a core comprising living packaging cells that secrete the viral vector, wherein the viral vector is a retroviral vector, the vector comprising a heterologous gene encoding a biologically active molecule operably linked to a promoter that regulates expression of the biologically active molecule in said cell, the heterologous gene being no more than 8 kb in length; and an external jacket surrounding said core, said jacket comprising a biocompatible material, said material having a porosity selected to permit passage of retroviral vectors of 100 nm diameter thereacross, permitting release of the viral vector from the capsule.

8. The method of claim 7 wherein the core additionally comprises a matrix, the packaging cells being immobilized by the matrix.

9. The method of claim 7 wherein the jacket comprises a hydrogel or thermoplastic material.

10. The method of claim 7 wherein the gene encodes a biologically active molecule selected from the group consisting of anti-proliferative agents, apoptosis-inducing molecules, bacterial toxins, tumor suppressor molecules, and anti-apoptotic molecules.

11. The method of claim 7 wherein said viral vector comprises a gene useful in the treatment of human tumors or cancers, or cell proliferation disorders.

12. The method of claim 7 wherein the viral vector is a replication deficient retroviral vector.

13. The method of claim 7 wherein said viral vector comprises a gene selected from the group consisting of GMCSF and HSV-tk and which method further comprises administration of ganciclovir to the cell.

14. The method of claim 7 wherein the capsule further comprises a tether for the retrieval of said capsule, and the method comprises the additional step of removing the capsule from proximity with the cell after delivery of the retroviral vector.

15. The method of claim 7 wherein the packaging cells are conditionally immortalized.

16. A method of delivering a viral vector to a cell by placing at least one capsule in proximity with the cell, said capsule comprising:

a core comprising living packaging cells that secrete the viral vector, wherein the viral vector is a retroviral vector, the vector comprising a heterologous gene encoding a biologically active molecule operably linked to a promoter that regulates expression of the biologically active molecule in said cell, wherein the heterologous gene is HSV-tk; and an external jacket surrounding said core, said jacket comprising a biocompatible material, said material having a porosity selected to permit passage of retroviral vectors of 100 nm diameter thereacross, permitting release of the viral vector from the capsule.

17. The method of claim 16 wherein the core additionally comprises a matrix, the packaging cells being immobilized by the matrix.

18. The method of claim 16 wherein the jacket comprises a hydrogel or thermoplastic material.

19. The method of claim 16 wherein the capsule is placed in proximity with the cell in vitro.

20. The method of claim 16 wherein the capsule further comprises a tether for the retrieval of said capsule, and the method comprises the additional step of removing the capsule from proximity with the cell after delivery of the retroviral vector.

21. The method of claim 16 wherein the packaging cells are conditionally immortalized.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 33 base pairs
      (B) TYPE: nucleic acid
      (C) STRANDEDNESS: single
      (D) TOPOLOGY: linear    (ii) MOLECULE TYPE: cDNA    (iii) HYPOTHETICAL: NO    (iv) ANTI-SENSE: NO    (xi) SEQUENCE DESCRIPTION: SEQ ID NO:1:

TTTAAGCTTC GCCACCATGC CGCACGCTGG GAG          33

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear    (ii) MOLECULE TYPE: cDNA    (iii) HYPOTHETICAL: NO    (iv) ANTI-SENSE: NO    (xi) SEQUENCE DESCRIPTION: SEQ ID NO:2:

TTTAAGCTTT CACTTGTGGC TCAGATAGGC          30